US00PP23780P3

(12) United States Plant Patent
Cain et al.

(10) Patent No.: US PP23,780 P3
(45) Date of Patent: Jul. 30, 2013

(54) PLUM TREE NAMED 'SUPLUMFORTYTHREE'

(50) Latin Name: *Prunus salicina*
Varietal Denomination: Suplumfortythree

(75) Inventors: David W. Cain, Bakersfield, CA (US); Terry A. Bacon, Bakersfiled, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 13/373,324

(22) Filed: Nov. 10, 2011

(65) Prior Publication Data

US 2013/0125273 P1 May 16, 2013

(51) Int. Cl.
*A01H 5/00* (2006.01)

(52) U.S. Cl.
USPC ..... Plt./184

(58) Field of Classification Search
USPC ..... Plt./184
See application file for complete search history.

*Primary Examiner* — Annette Para
(74) *Attorney, Agent, or Firm* — Knobbe, Martens, Olson & Bear, LLP

(57) ABSTRACT

A new and distinct plum tree variety, *Prunus salicina*, cv. 'Suplumfortythree' is characterized by red flesh, black skin, firm fruit, with a medium bloom and ripening in the middle of the season

1 Drawing Sheet

Latin name of the genus and species claimed: *Prunus salicina.*

Variety denomination: 'Suplumfortythree'.

BACKGROUND AND SUMMARY OF THE INVENTION

This invention relates to the discovery and asexual propagation of a new and distinct variety of plum, *Prunus salicina* cv. 'Suplumfortythree'. The new variety was first hybridized in March 1997 by David W. Cain and selected in August 2000 by Terry Bacon as breeder number: '97P040-010-244'. The new variety was first evaluated by Terry Bacon near Wasco, Calif. in Kern County. The variety 'Suplumfortytfour' was originated by hybridization.

The new variety 'Suplumfortythree' is characterized by red flesh with black skin.

The seed parent is '93P-007' (unpatented), and the pollen parent is '90P-055' (unpatented). The parent varieties were first crossed in March of 1997, with the date of sowing being January 1998, and the date of first flowering being March 1999. The new plum variety 'Suplumfortythree' was first asexually propagated by Terry Bacon near Wasco, Kern County, Calif. in January 2002, by budding.

The new variety 'Suplumfortythree' is distinguished from its seed parent, '93P-007' (unpatented), in that while both of the varieties ripen at a similar time, '93P-007' has amber flesh compared to red flesh for the new variety.

The new variety 'Suplumfortythree' is distinguished from its pollen parent, '90P-055' (unpatented), in that both varieties have red flesh but '90P-055' ripe date is July 1$^{st}$ while the new variety ripe date is August 1$^{st}$.

The new variety 'Suplumfortythree' has a similar ripening time as 'Friar' (unpatented), but has red flesh compared to amber flesh for 'Friar.'

The new variety 'Suplumfortythree' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new plum variety 'Suplumfortythree'. The illustration shows the upper and lower surface of the leaves, an exterior and sectional view of a fruit divided across its suture plane to show flesh color, pit cavity and the stone remaining in place. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 13 year old 'Suplumfortythree' plants on 'Nemaguard' (unpatented) rootstock, grown in the vicinity of Wasco, Kern County, Calif., during 2010, and is believed to apply to plants of the variety grown under similar conditions of soil and climate elsewhere.

TREE

General: (Measurements taken on 13 year old tree unless otherwise noted.).

*Size.*—Medium. Normal for most plum varieties. Reaches a height of approximately 3-5 meters with normal pruning.

*Spread.*—Approximately 3-5 meters.

*Vigor.*—Moderately vigorous, about 1.5 to 2 meters in height the first growing season.

*Growth*.—Semi-upright.
*Productivity*.—Productive.
*Form*.—Vase formed.
*Bearer*.—Regular.
*Fertility*.—Unknown, should be planted with another variety to ensure consistent production.
*Canopy density*.—Medium.
*Hardiness*.—Hardy in all fruit growing areas of California. Winter chilling requirement is approximately 600 hours at or below 7.2° C.
*Disease resistance/susceptibility*.—Under close observation in Kern County, Calif., no particular plant/fruit disease resistance/susceptibility has been observed.
*Insect resistance/susceptibility*.—Under close observation in Kern County, Calif., no particular plant/fruit insect resistance/susceptibility has been observed.

Trunk: (Measurements at approximately 30 cm above soil line on mature tree).
*Diameter*.—Approximately 18 cm, varies with soil type, fertility, climatic conditions and cultural practices.
*Texture*.—Medium shaggy, increases with age of tree.
*Trunk color*.—About Medium Grey-Brown 199B to Brown 200B; becomes darker with age.

Branches: (Measurements at approximately 90 cm above soil line.).
*Size*.—Diameter approximately 7 to 9 cm.
*Texture*.—Smooth on first year wood and increasing roughness with tree age.
*Color*.—Varying from about Medium Grey-Brown 199B to Brown 200B.
*Lenticels*.—Present.

Lenticels:
*Number*.—Numerous.
*Density*.—about 2/cm$^2$ but varies with tree vigor and climatic conditions.
*Color*.—About Medium Grey-Brown 199B.
*Size*.—Medium.
*Length*.—3 mm.
*Width*.—2 mm.

Flowering shoots: (Data taken in July at mid-point of season growth.).
*Size*.—Average diameter approximately 5 mm.
*Color*.—Topside: About Medium Yellow-Green 152A. Underside: About Medium Yellow-Green 152A.
*Internode length*.—Medium; approximately 2 cm. Midway on flowering shoot.
*Flowering shoot lenticels*.—Medium amount. Color: About Medium Grey-Brown 199B. Diameter: Approximately 1.0 mm.
*Flowering shoot leaf buds*.—Shape: Obovate. Width: Approximately 1.5 mm. Length: Approximately 2.1 mm. Color: About Dark Greyed-Orange 177A.
*Flowering shoot flower buds*.—Shape: Elliptic. Width: Approximately 1 mm. Length: Approximately 1.8 mm. Color: About Dark Greyed-Orange 177A. Number of buds per node: Usually 2.
*Density of buds*.—Medium.
*Flower bud distribution*.—On spurs and one year old shoots.
*Ratio of wood (leaf) buds to flowering buds*.—½ on nodes.
*Anthocyanin intensity*.—None or very slight.

FOLIAGE

Leaves: (Data taken in July on fully expanded leaves at mid-point of the season growth).
*Size*.—Medium.
*Average length*.—Medium; approximately 100 mm.
*Average width*.—Medium; approximately 55 mm.
*Thickness*.—Medium.
*Color*.—Upper surface: About Dark Green 131A. Lower surface: About Medium Green 137D.
*Form*.—Broad obovate.
*Tip*.—Cuspidate.
*Base*.—Irregularly V-shaped.
*Margin*.—Crenate.
*Venation*.—Pinately net veined.
*Vein color*.—About Medium Yellow-Green 146D.
*Surface texture*.—Smooth.
*Leaf blade (ratio of length to width)*.—2:1.
*Shape in the cross section*.—Flat.
*Angle at apex*.—Small.
*Profile*.—Flat.
*Leaf blade tip*.—Slightly curved downwardly.
*Angle of tip*.—Acute.
*Undulation of margin*.—Slight.

Petiole:
*Average length*.—Medium; approximately 13 mm.
*Average diameter*.—Approximately 1.5 mm.
*Color*.—About Medium Yellow-Green 146D but can be darker with more light exposure.

Stipules:
*Number/leaf bud*.—Approximately 1 per leaf bud when present.
*Typical length*.—Approximately 3 mm.
*Color*.—About Medium Greyed-Orange 164B.
*Persistence*.—Falls off.

Leaf glands:
*Form*.—Globose.
*Average number*.—Usually 2.
*Position*.—On petiole/leaf base transition area, alternate.
*Average size*.—Small; approximately 0.5 mm.
*Color*.—About Dark Grey-Brown 199B.

FLOWERS

General:
*Flower blooming period*.—First bloom: Approximately Feb. 24, 2010. Full bloom: Approximately Feb. 28, 2010.
*Location of first bloom*.—Older wood.
*Location of full bloom*.—Uniform throughout the canopy.
*Time of bloom*.—Medium.
*Duration of bloom*.—Medium; approximately 12 days.
*Diameter of fully opened flower*.—Medium, approximately 10 mm.
*Flower aroma*.—Very slight aroma.
*Shape*.—Rosaceous.

Peduncle:
*Length*.—Medium; approximately 10 mm.
*Diameter*.—Medium; approximately 1 mm.
*Color*.—About Medium Yellow-Green 144B.
*Pubescence*.—Absent.

Petals:
*Number*.—5.
*Arrangement*.—Overlapping slightly.
*Length*.—Approximately 12 mm.
*Diameter*.—Approximately 10 mm.
*Shape*.—Obovate.
*Apex shape*.—Rounded.
*Base shape*.—Narrows at point of attachment.
*Color of inner and outer surface*.—White.
*Surface texture*.—Smooth.
*Margins*.—Slightly undulating.
*Frequency of flowers with double petals*.—None.
*Size*.—Medium, about 10 mm wide.
*Claw length*.—Medium.
*Margin waviness*.—Medium.
*Base angle*.—Narrow.
*Division of upper margin*.—Entire.
*Pubescence of inner surface*.—Absent.
*Pubescence of outer surface*.—Absent.

Sepals:
*Number*.—5.
*Length*.—Approximately 3 mm.
*Diameter*.—Approximately 2 mm.
*Shape*.—Elliptic.
*Color*.—About Medium Yellow-Green 144A.
*Surface texture*.—Smooth.
*Margins*.—Entire.
*Positioning*.—Adpressed to petals.
*Pubescence of inner surface*.—Absent.
*Pubescence of outer surface*.—Absent.
*Frequency of flowers with double sepals*.—None.

Stamens:
*Number*.—Ranges from about 20 to about 30, average 25.
*Average length*.—About 7 mm.
*Filament color*.—White.
*Anther color*.—About Medium Greyed-Orange 167A after starting to dry.
*Flower pollen color*.—About Light Greyed-Orange 163C when first opened.
*Position*.—Perigynous.

Pistil:
*Number*.—Usually one.
*Average length*.—Approximately 9 mm.
*Ovary diameter*.—Approximately 0.5 mm.
*Pubescence*.—None.
*Stigma extension in comparison to anthers*.—Level or slightly above anthers.
*Style frequency of supplementary pistils*.—Absent.

Flower buds:
*Hardiness*.—Hardy.
*Size*.—Medium.
*Length*.—Medium.
*Shape*.—Pointed.
*Positioning*.—Slightly free.
*Pubescence*.—Absent.
*Color*.—About Dark Greyed-Orange 177A.

Receptacle:
*Depth*.—Medium
*Pubescence of inner surface*.—Absent.
*Pubescence of outer surface*.—Absent.

FRUIT

General: (Description taken near Wasco, Kern County, Calif. on Aug. 1, 2010).
*Date of first pick*.—Approximately Jul. 28, 2010.
*Date of last pick*.—Approximately Aug. 7, 2010.
*Maturity when described*.—Firm.
*Season ripening*.—Medium.
*Position of maximum diameter*.—Towards the middle.
*Symmetry about the suture*.—Symmetric.

Size:
*Length* (*stem end to apex*).—Approximately 55 mm.
*Diameter in line with suture plane*.—Approximately 55 mm.
*Diameter perpendicular to suture plane*.—Approximately 63 mm.
*Average weight*.—Approximately 128 gm.

Form:
*Viewed from apex*.—Rounded, symmetrical.
*Viewed from side, facing suture*.—Rounded, slightly flattened, symmetrical.
*Viewed from side, perpendicular to suture*.—Rounded, slightly flattened, symmetrical.

Apex shape: Flattened.
Apex base: Rounded.

Fruit stem cavity:
*Shape*.—Flaring.
*Depth*.—Medium; Approximately 8 mm.
*Breadth*.—Approximately 8 mm.
*Width*.—Narrow.

Fruit stem:
*Length*.—Medium; approximately 8 mm.
*Diameter*.—Approximately 2 mm.
*Color*.—About Medium Green 143C.
*Adherence to stone*.—Medium.

Fruit skin:
*Thickness*.—Medium.
*Adherence to flesh*.—Medium.
*Surface texture*.—Medium.
*Pubescence*.—None.
*Bloom*.—Slight.
*Ground color*.—Not visible.
*Overcolor*.—About Black 202A covering 100% f the fruit skin
*Taste*.—Mildly Tart.
*Reticulation*.—Absent.
*Roughness*.—Absent.
*Tenacity*.—Tenacious to flesh.
*Tendency to crack*.—Slight.

Flesh:
*Ripens*.—Evenly.
*Texture*.—Fine-juicy.
*Fibers*.—Medium.
*Flavor*.—Sweet-tart.
*Brix*.—Approximately 22°.
*Juice*.—Abundant to moderate.
*Aroma*.—Slight.
*Color*.—Ranging from Medium Red 47C to Darker Red 46B.
*Anthocyanin color under skin*.—Strongly expressed.
*Anthocyanin color of flesh*.—Strongly expressed.
*Anthocyanin color around stone*.—Strongly expressed.
*Amygdalin*.—Wanting.

*Acidity*.—Medium-high.
*Sugar content*.—High.
*Eating quality*.—Good.
*Stone/flesh ratio*.—1/30.
*Firmness*.—Medium.

Pit cavity size:
*Length*.—Approximately 20 mm.
*Diameter perpendicular to suture plane*.—Approximately 10 mm.
*Diameter in line with suture*.—Approximately 20 mm.

Fruit use: Fresh market.

Fruit shipping and keeping quality: Medium.

Stone:
*Stone freeness*.—Semi-free.
*Degree of adherence to flesh*.—Weak.
*Stone size*.—Size: Small. Size compared to Fruit: Small. Length: Medium, approximately 20 mm. Diameter in line with suture plan: Approximately 20 mm. Diameter perpendicular to suture plane: Approximately 10 mm. Width of Stalk End: Medium. Angle of Stalk end: Acute angle. Hilum: Oval.
*Stone form*.—Viewed from side: Nearly round to slightly obovate. Viewed from ventral end: Flattened, symmetrical. Viewed from Stem end: Flattened, symmetrical.
*Stone shape*.—Base shape: Nearly straight. Apex shape: Rounded with small sharp point.
*Stone surface*.—Somewhat smooth with sharp ridges running from base to apex.
*Stone halves*.—Nearly symmetrical.
*Stone ridges*.—Continuous.
*Stone outgrowing keel*.—Well-developed.
*Stone tendency to split*.—Almost none.
*Stone color*.—About Light Greyed-Orange 164C when dried.
*Position of maximum*.—Middle.
*Sides*.—Nearly equal.
*Pits*.—Angular.
*Fibers*.—Parts from flesh smoothly.
*Ventrical edge*.—Medium.
*Dorsal edge*.—Narrow.
*Ground color*.—Not visible.
*Extent of overcolor*.—Very large.
*Pattern of overcolor*.—None.

Suture:
*Line*.—Shallow.

Ventral surfaces:
*Lips*.—Nearly equal.
*Depression of apex*.—Indistinct.
*Pistil base*.—Not persisting.
*Pubescence at apex*.—Absent.

Pistil point:
*Shape*.—Flattened.

What is claimed is:

1. A new and distinct plum tree as herein described and illustrated.

* * * * *

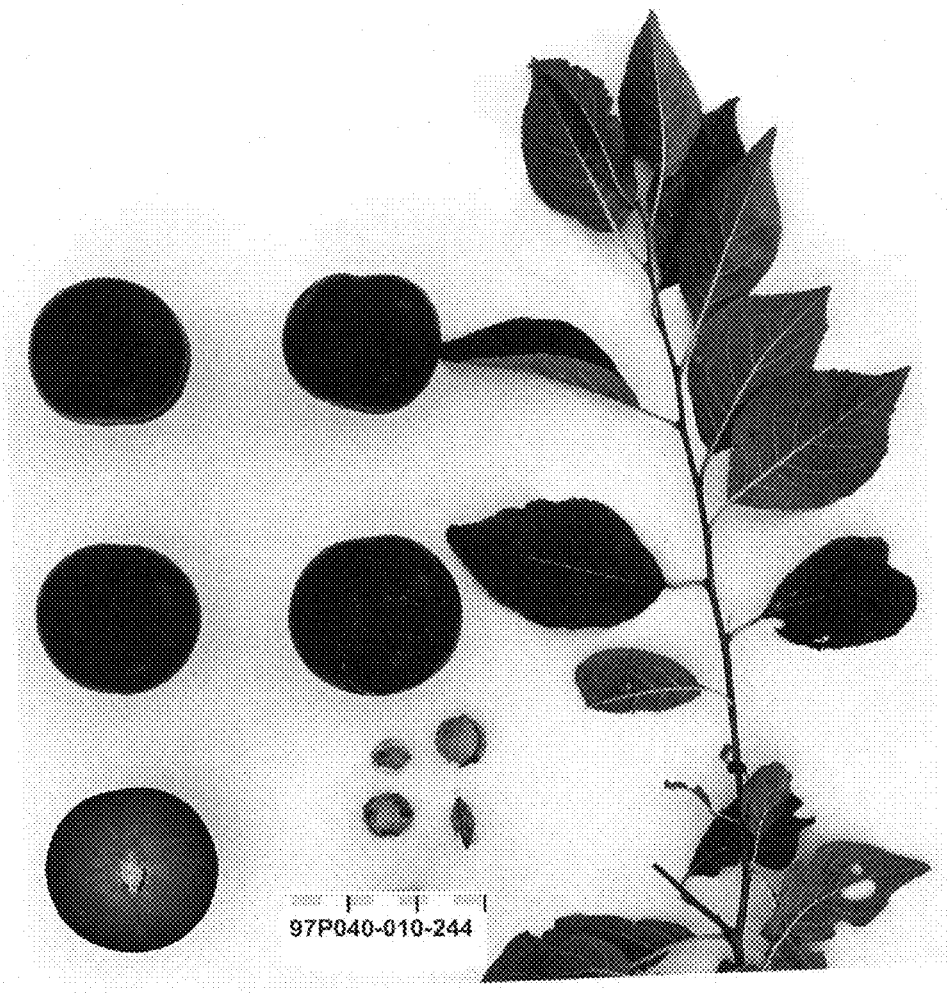
97P040-010-244